(12) United States Patent
Korner et al.

(10) Patent No.: US 7,815,587 B2
(45) Date of Patent: Oct. 19, 2010

(54) BELOW-KNEE ORTHOSIS

(75) Inventors: Doris Korner, Gottingen (DE); Alexander Von Ascheberg, Duderstadt (DE)

(73) Assignee: Otto Bock HealthCare IP GmbH & Co., KG, Duderstadt (DE)

( * ) Notice: Subject to any disclaimer, the term of this patent is extended or adjusted under 35 U.S.C. 154(b) by 0 days.

(21) Appl. No.: 11/563,948

(22) Filed: Nov. 28, 2006

(65) Prior Publication Data

US 2007/0135746 A1    Jun. 14, 2007

(30) Foreign Application Priority Data

Dec. 8, 2005  (DE) .................. 10 2005 058 999

(51) Int. Cl.
*A61F 5/00* (2006.01)
(52) U.S. Cl. ............... 602/27; 602/5; 602/23; 128/882
(58) Field of Classification Search ............ 602/27, 602/5, 6, 23, 28, 29; 128/882
See application file for complete search history.

(56) References Cited

U.S. PATENT DOCUMENTS

| 5,460,600 | A | * | 10/1995 | Bieling ............... 602/27 |
| 5,817,041 | A | * | 10/1998 | Bader ............... 602/23 |
| 6,302,858 | B1 |  | 10/2001 | DeToro et al. |
| 6,406,500 | B1 |  | 6/2002 | Phillips |
| 2004/0134500 | A1 | * | 7/2004 | Ingimundarson et al. ..... 128/882 |
| 2004/0186401 | A1 | * | 9/2004 | Guenther ............... 602/16 |

FOREIGN PATENT DOCUMENTS

| DE | 299 08 981 U1 | 5/1999 |
| GB | 2 139 089 A | 11/1984 |
| WO | WO 01/01896 | 11/2001 |
| WO | WO 02/096328 | 12/2002 |

OTHER PUBLICATIONS

European Search Report dated Feb. 15, 2007.

* cited by examiner

*Primary Examiner*—Patricia M Bianco
*Assistant Examiner*—Keri J Nicholson
(74) *Attorney, Agent, or Firm*—Whitham Curtis Christofferson & Cook, PC

(57) ABSTRACT

A below-knee orthosis with fastening devices for fastening the orthosis to the foot and to the lower leg includes an L-shaped support spring made of a resilient material. The L-shaped support spring has an upright branch that defines a contact plane, and is intended to bear on the dorsal aspect of the lower leg. The lower end of the upright branch is adjoined by a horizontal branch designed to engage under the foot. The below-knee orthosis allows for an improved heel-to-toe behavior in the material of the support spring which takes into account the natural outward position of the foot by the upright branch being twisted in the lower area in such a way that the horizontal branch continuing the lower end is turned outward by an angle α from the plane lying perpendicular to the contact plane of the upright branch above the twisted lower area.

12 Claims, 4 Drawing Sheets

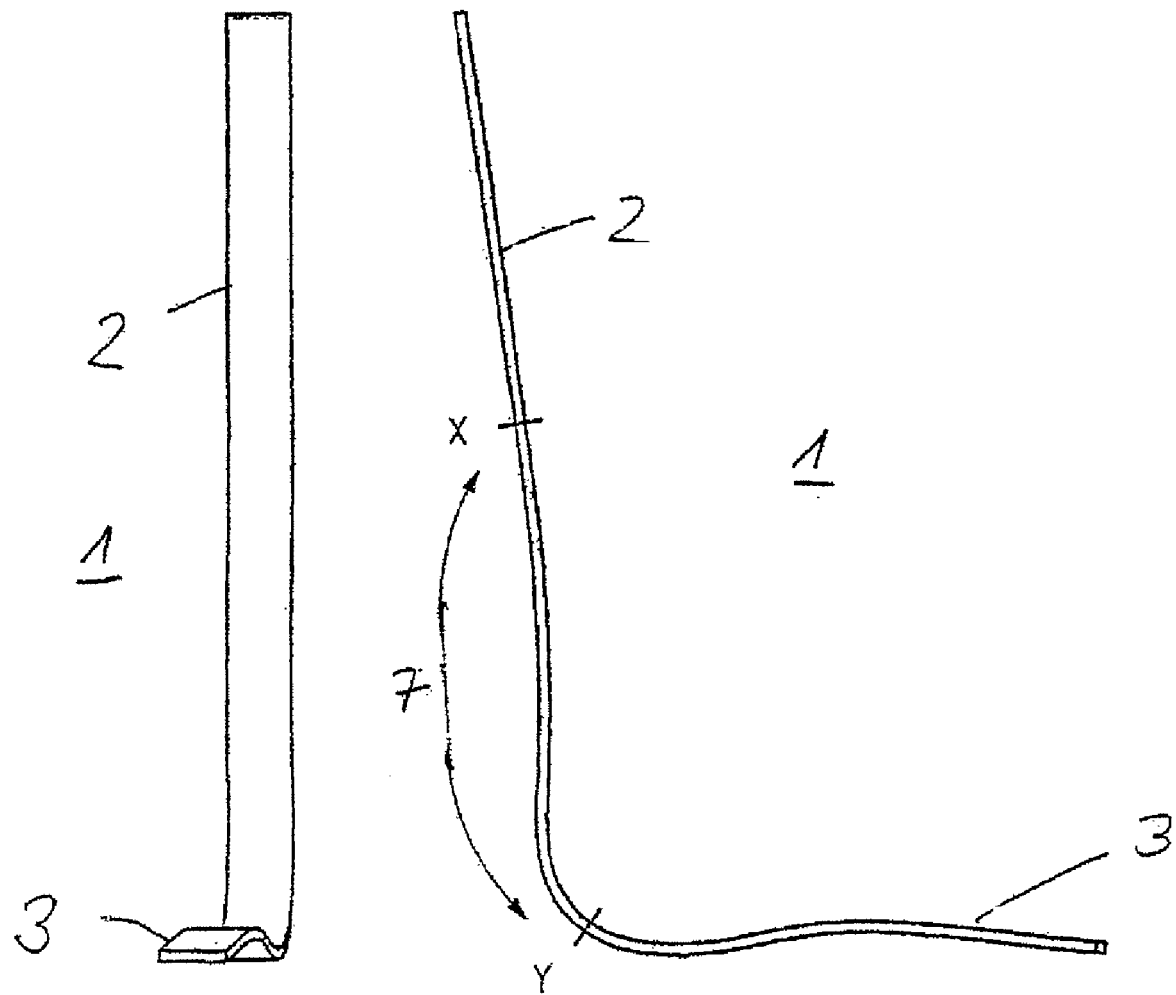

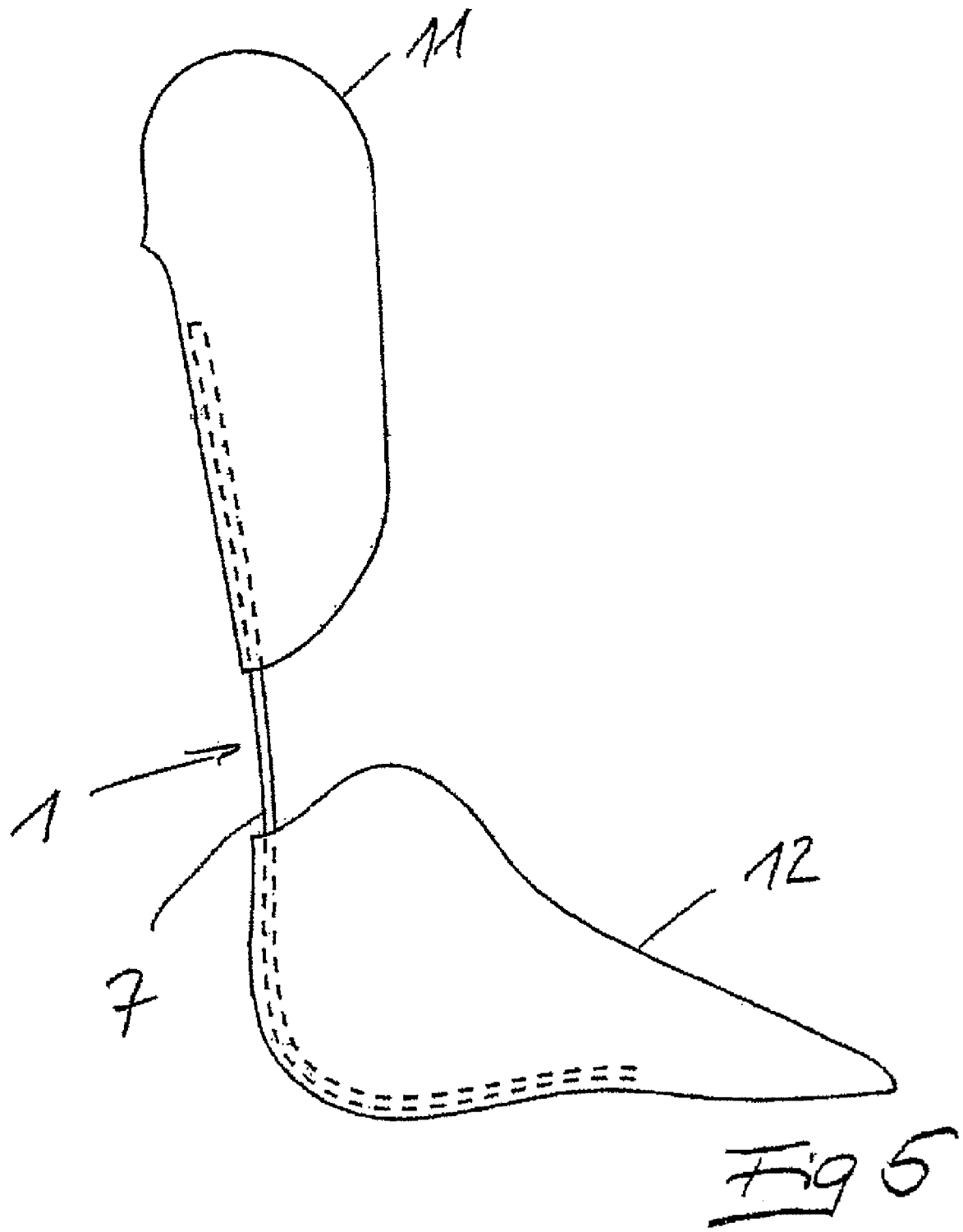

BELOW-KNEE ORTHOSIS

FIELD OF THE INVENTION

The invention relates to a below-knee orthosis with fastening devices for fastening the orthosis to the foot and to the lower leg, and with an L-shaped support spring which is made of a resilient material and which has an upright branch that defines a contact plane and is intended to bear on the dorsal aspect of the lower leg, the lower end of which upright branch is adjoined by a horizontal branch designed to engage under the foot.

BACKGROUND OF THE INVENTION

This type of design of a below-knee orthosis has been known for a long time. The resilient flat material forming the support spring can be formed by a spring steel, but preferably by a fiber-reinforced plastic.

The support springs made of a resilient flat material form a substantially right angle when seen in a side view, both the upright branch and the horizontal branch having areas where they bend out from the plane of the flat material in order to permit adaptation to the anatomical circumstances. Moreover, the transition between the upright branch and the horizontal branch is rounded. In terms of its branches, the support spring is designed symmetrically with respect to a vertical mid-plane, which is readily achieved through using a resilient flat material.

The anatomy of the ankle joint has the effect that, when a person is standing still, the foot assumes an outward position, which is of the order of magnitude of 7° relative to the sagittal plane. In the course of movement in the walking cycle, a rotation of the tibia takes place that further increases the outward position of the foot, with the result that it can amount to 7 to 12° or more. This outward position of the foot is not taken account of by known functional orthoses of simple design.

BRIEF SUMMARY OF THE INVENTION

The object of the invention is therefore to design a simple below-knee orthosis of the aforementioned type in such a way that, while maintaining a good function, it takes account of the natural outward position of the foot.

According to the invention, this object is achieved, in a below-knee orthosis of the aforementioned type, by the fact that the upright branch is twisted in the lower area in such a way that the horizontal branch continuing the lower end is turned outward by an angle α from the plane lying perpendicular to the contact plane of the upright branch above the twisted lower area.

The contact plane defined by the upright branch generally lies parallel to the frontal plane of the patient. According to the invention, the upright branch, in a lower area that includes the ankle area, is gradually twisted in such a way that the horizontal branch adjoining the lower end perpendicularly is located in the desired outward position. The imaginary bend line, which is located approximately at the lower end of the upright branch, and about which the horizontal branch can move relative to the upright branch during loading by virtue of the elasticity of the material, thus does not lie in the contact plane (frontal plane) but instead is already turned outward from this plane by the angle α. This ensures that the horizontal branch can still adjoin the lower end of the upright branch in a perpendicular manner.

This is especially important when using a fiber-reinforced plastic whose fiber composite comprises mutually parallel fibers which extend in the longitudinal direction of the support spring and which, when angled away from a bend plane (by the movement of the horizontal branch relative to the upright branch), would otherwise be moved relative to one another during the heel-to-toe motion and could cause delamination of the fiber-reinforced plastic material.

According to the invention, therefore, the upright branch, which in the upper area defines a contact plane lying perpendicular to a mid-plane (sagittal plane), is twisted in the lower area in such a way that the horizontal branch lying perpendicular to the upright branch at the lower end adopts the angle for centrally supporting the foot in the natural outward position, The upright branch can thus be arranged centrally on the dorsal aspect of the lower leg. The twisting, by means of which the outward position of the horizontal branch is brought about, takes place in a lower area (bend area) in which the upright branch extends level with the Achilles tendon. The outward position of the foot is thus taken into account in the area of the upright branch of the support spring, so that the bend line between horizontal branch and upright branch is already turned out from the contact plane by the angle of the desired outward position of the foot.

In a preferred and simple embodiment, the material of the support spring is a flat material whose large top face in the upper area of the upright branch defines the contact plane and is twisted in the lower area by the angle α relative to the contact plane, so that the horizontal branch can adjoin the lower end in a manner perpendicular to the surface of the upright branch and thereby assumes the desired angle for the outward position of the foot.

Although the orthosis according to the invention thus deforms about an imaginary bend line between upright branch and horizontal branch during the heel-to-toe motion, thus sparing the material of the orthosis, a movement between lower leg and foot is obtained which is transmitted via the contact plane of the upright branch, so that the movement plane for the supported foot extends parallel to the frontal plane and thereby corresponds to the natural movement in the ankle joint.

BRIEF DESCRIPTION OF THE DRAWINGS

The invention will be explained in more detail below on the basis of an illustrative embodiment depicted in the drawing, in which:

FIG. 2 shows a side view of the support spring;

FIG. 3 shows a front view of the support spring;

FIG. 5 shows a schematic representation of a below-knee orthosis constructed with a support spring according to the invention.

DETAILED DESCRIPTION OF THE INVENTION

Figure 1:
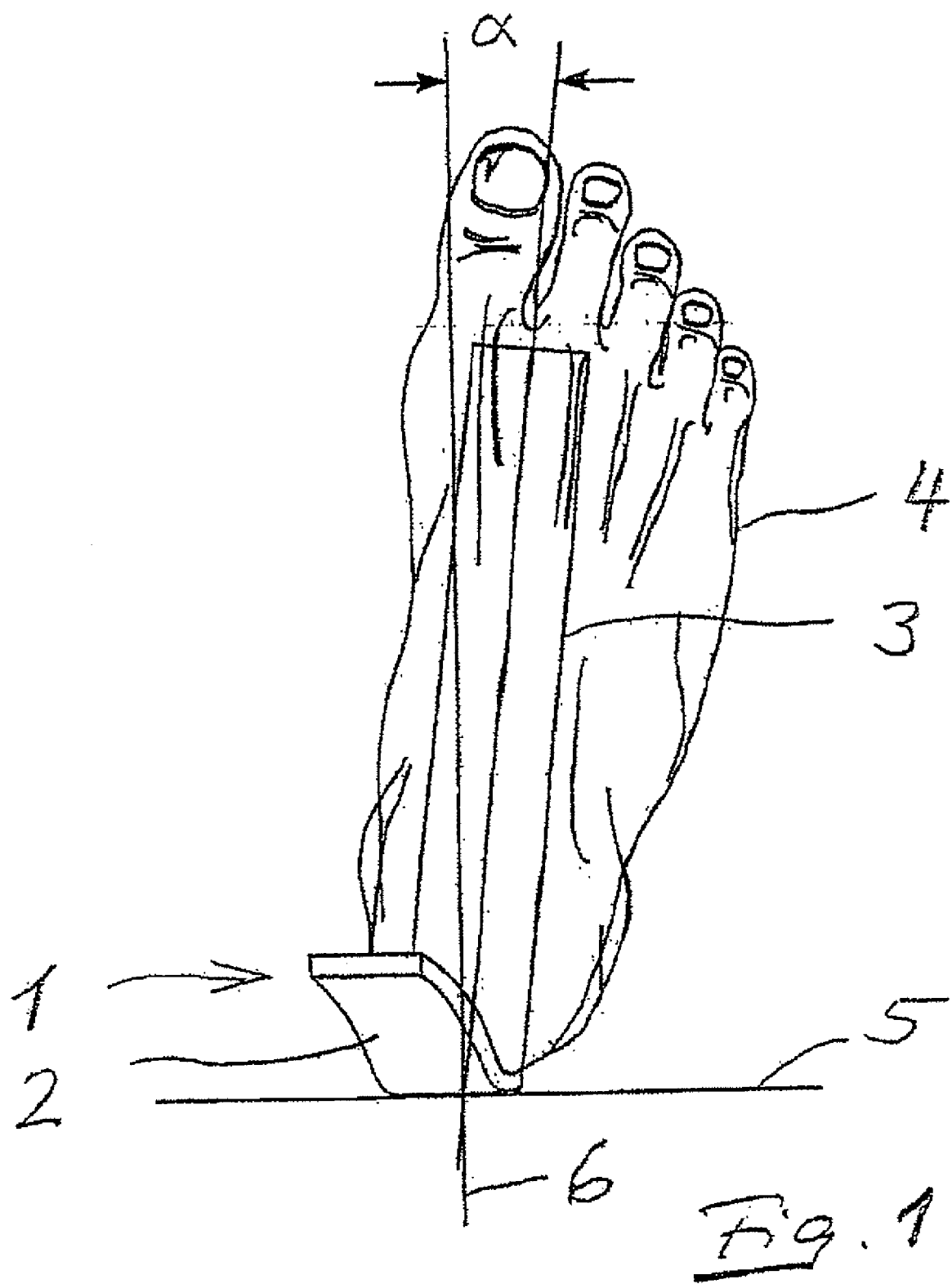
FIG. 1 shows a schematic representation of a support spring according to the invention in relation to a foot of the person wearing the orthosis.

For reasons of clarity, the drawing does not show the fastening means that are provided on a support spring 1 in order to form a below-knee orthosis and that fasten it to the lower leg and foot. Numerous configurations of these are known to a person skilled in the art. As the drawing illustrates, the support spring 1 is composed of an upright branch 2, and of a substantially horizontal branch 3 intended to engage under a foot 4 of the person wearing the orthosis.

FIG. 1 indicates a frontal plane 5 and a sagittal plane 6 of the person wearing the orthosis. The upright branch 2 lies with its upper end parallel to the frontal plane 5, to which the sagittal plane 6 is perpendicular. When the person wearing the orthosis is standing on both legs, the foot 4 assumes the position shown in FIG. 1, that is to say its longitudinal axis is turned outward by an angle $\alpha$, for example of 7°.

Accordingly, the horizontal branch 3 of the support spring 1 is also turned outward by the angle $\alpha$.

As FIGS. 2 and 3 illustrate, the twisting of the horizontal branch 3 is achieved by the fact that the upright branch 2, in a lower area 7 lying between the points X and Y shown in FIG. 2, is slightly twisted helically about the vertical axis. Starting from the point X (start of the bend area), the upright branch 2 merges into a torsion, through which the turning by the angle $\alpha$ takes place as far as the point Y. At the point Y, the upright branch 2 merges smoothly into the horizontal branch 3.

The drawing also illustrates that, in the bend area 7, the upright branch, seen from the front, has a concave curvature that simulates the profile in the malleolar region of a foot. By contrast, the transition area (around the transition point Y) has a convex curvature, in order to ensure a uniform transition for the longitudinal fibers in the resilient flat material. Seen from above, the horizontal branch 3 has a convex curvature corresponding to the profile of the sole of the foot 4.

In the illustrative embodiment shown, the material of the support spring 1 is a flat material that preferably has a width of 15 to 40 mm and a thickness of 2 to 12 mm. The bend area 7 should not be less than a certain minimum height, to ensure that the twisting takes place uniformly and gradually and does not weaken the statics of the upright branch 2. The length of the bend area is preferably between 3 and 20 cm.

Above the bend area 7, the orientation of the material of the support spring 1 defines the contact plane for the lower leg. This contact plane is substantially parallel to the frontal plane of the patient, as is illustrated in FIG. 4.

Figure 4:
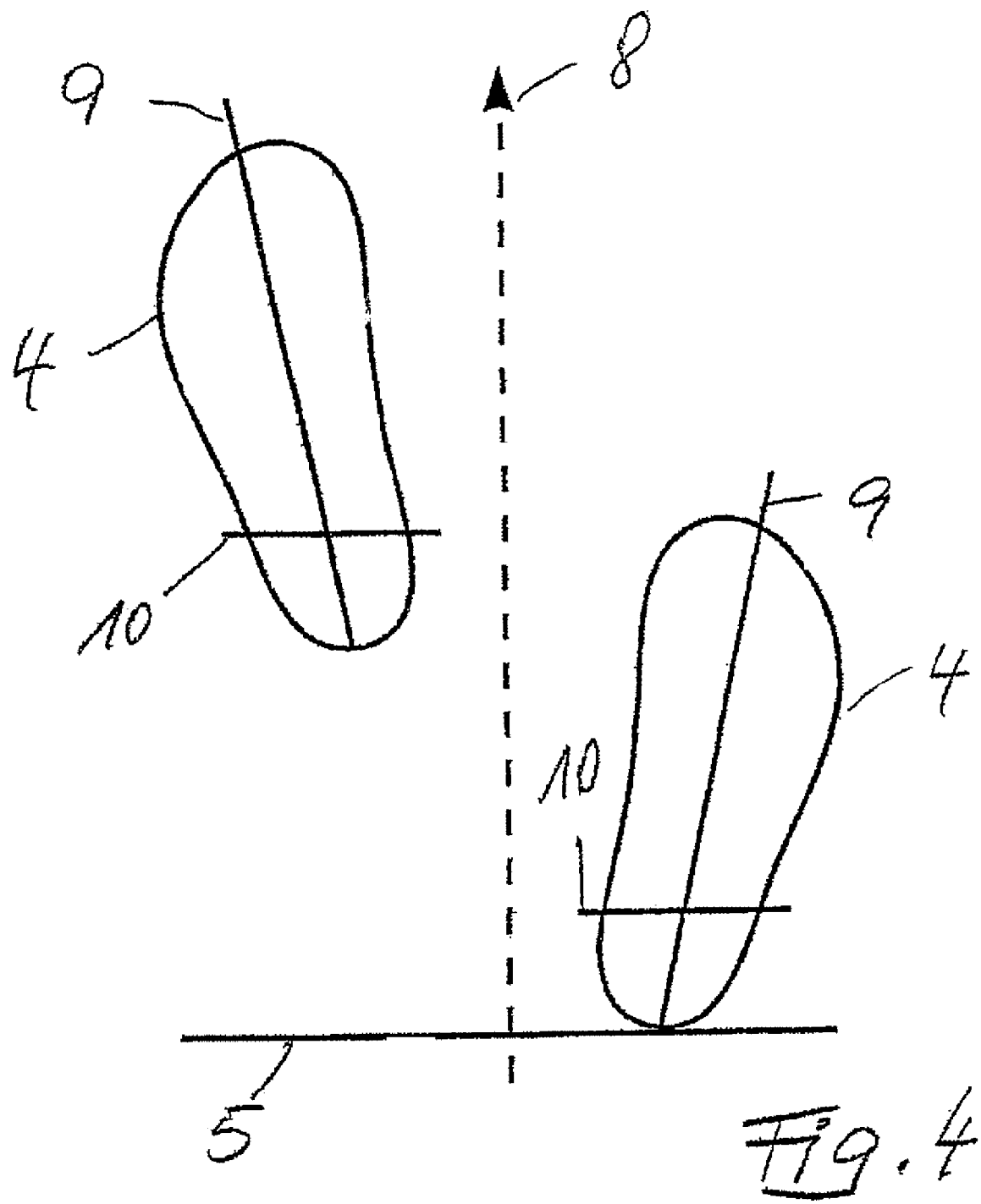
FIG. 4 shows a schematic depiction of the resulting outward position of the foot.

FIG. 4 shows schematically the stepping direction 8 followed by a human when walking. The stepping direction is substantially determined by the sagittal plane of the human body. The feet 4 move on both sides of the plane defined by the stepping direction 8, the outward position of the foot being obtained at the heel-down phase, resulting in a foot axis 9 that is oblique with respect to the stepping direction 8.

According to the position of the natural axis of the ankle, the orthosis supports a pivot axis 10, for the heel-to-toe motion of the foot 4, lying parallel to the frontal plane 5. The pivot axis 10 arises from the movement of the contact plane of the upright branch 2 formed above the bend area 7 in its movement relative to the horizontal branch 3.

The orthosis shown in FIG. 5, and constructed with the support spring 1 according to the invention, is supplemented by a fastening shell 11 for the calf area of the lower leg and by a fastening shell 12 for the foot area. The support spring 1 is connected to the fastening shells 11, 12 in a rotationally fixed manner. Other fastening means, for example in the form of velcro tapes, for fixing the lower leg and foot to the fastening shells 11, 12 are not shown.

In the illustrative embodiment according to FIG. 5, the fastening shell 11 for the lower leg extends to about the start of the bend area 7 of the support spring 1, thereby substantially covering the contact plane for the lower leg.

The invention claimed is:

1. A below-knee orthosis with fastening devices for fastening said orthosis to a foot and to a lower leg, comprising:
    an L-shaped support spring made of a resilient material comprising an upright branch and a horizontal branch joined at a bend area,
    wherein said upright branch of said L-shaped support spring defines a contact plane for bearing on a dorsal portion of said lower leg,
    wherein the horizontal branch is designed for engagement under said foot, and
    wherein said upright branch is twisted helically about a vertical axis in a lower area such that said horizontal branch is turned outward by an angle $\alpha$ from a plane lying perpendicular to said contact plane of said upright branch above said lower area.

2. The below-knee orthosis a claimed in claim 1, wherein said fibers are carbon fibers.

3. The below-knee orthosis as claimed in claim 1, wherein said fibers are glass fibers.

4. The below-knee orthosis as claimed, in claim 1, wherein said fibers are polyester fibers.

5. The below-knee orthosis as claimed in claim 1, wherein said fibers are composed of a mixture of different fiber types.

6. The below-knee orthosis as claimed in claim 1, wherein said resilient material of said support spring is a flat material.

7. The blow-knee orthosis as claimed in claim. 1, wherein said horizontal branch designed for engagement under said foot has a convex curvature corresponding the profile of the sole of the foot.

8. The below-knee orthosis as claimed in claim 1, wherein said upright branch defining a contact plane for bearing on a dorsal portion of said lower leg is angled.

9. The below-knee orthosis as claimed in claim 1, wherein said L-shaped support is configured to permit walking by as person using said below-knee orthosis.

10. The below-knee orthosis as claimed in claim 1, wherein a length of the bend area is between 3 and 20 cm.

11. The below-knee orthosis as claimed in claim 1, wherein the angle $\alpha$ is on the order of approximately 7°.

12. The below-knee orthosis as claimed in claim 1, wherein the resilient material of said support spring is a fiber-reinforced plastic having mutually parallel fibers extending along a length of said support spring.

* * * * *